(12) United States Patent
Choung et al.

(10) Patent No.: US 10,265,333 B2
(45) Date of Patent: Apr. 23, 2019

(54) LIPID NANOMATERIAL CONTAINING LYSOPHOSPHATIDYLCHOLINE OR DERIVATIVE THEREOF AND METHOD FOR PREPARING SAME

(71) Applicant: ARIBIO INC., Seoul (KR)

(72) Inventors: Jai Jun Choung, Soungnam-si (KR); Myung Hwa Kim, Yongin-si (KR); Du Jin Seol, Uiwang-si (KR); Sae Kwang Ku, Daegu (KR); Soo Hyun Sung, Seoul (KR); Young Sam Kim, Seoul (KR)

(73) Assignee: ARIBIO CO., LTD., Sungnam, Gyeonggi-Do (KR)

( * ) Notice: Subject to any disclaimer, the term of this patent is extended or adjusted under 35 U.S.C. 154(b) by 79 days.

(21) Appl. No.: 14/774,904

(22) PCT Filed: Mar. 11, 2014

(86) PCT No.: PCT/KR2014/002004
§ 371 (c)(1),
(2) Date: Sep. 11, 2015

(87) PCT Pub. No.: WO2014/142517
PCT Pub. Date: Sep. 18, 2014

(65) Prior Publication Data
US 2016/0022711 A1 Jan. 28, 2016

(30) Foreign Application Priority Data
Mar. 12, 2013 (KR) .......... 10-2013-0026030

(51) Int. Cl.
*A61K 31/685* (2006.01)
*A61K 9/00* (2006.01)
*A61K 9/107* (2006.01)
*A61K 9/51* (2006.01)

(52) U.S. Cl.
CPC .......... *A61K 31/685* (2013.01); *A61K 9/0019* (2013.01); *A61K 9/1075* (2013.01); *A61K 9/5123* (2013.01)

(58) Field of Classification Search
None
See application file for complete search history.

(56) References Cited

U.S. PATENT DOCUMENTS

| | | | |
|---|---|---|---|
| 2008/0145411 A1 | 6/2008 | Shinagawa et al. | |
| 2009/0281065 A1 | 11/2009 | Ramchand et al. | |
| 2010/0305218 A1* | 12/2010 | Wooster ............... | A61K 9/1075 514/784 |
| 2011/0135684 A1 | 6/2011 | Lotteau et al. | |
| 2013/0189316 A1* | 7/2013 | Chen .................... | A61K 9/1075 424/400 |

FOREIGN PATENT DOCUMENTS

| | | | |
|---|---|---|---|
| EP | 2740479 | * | 6/2014 |
| KR | 1020070063023 A | | 6/2007 |
| KR | 1020080110681 A | | 12/2008 |

OTHER PUBLICATIONS

International Search Report for International Application No. PCT/KR2014/002004, dated Jul. 24, 2014 (4 pages).

* cited by examiner

*Primary Examiner* — Tigabu Kassa
(74) *Attorney, Agent, or Firm* — Lucas & Mercanti, LLP

(57) ABSTRACT

The present invention relates to a lipid nanomaterial containing lysophosphatidylcholine or an ether derivative thereof, a method for preparing the same, a method for reducing erythrocyteolysis and hemagglutination using the compound, and a pharmaceutical agent containing the lipid nanomaterial. The present invention contains lysophosphatidylcholine or an ether derivative thereof as an active ingredient, and can be useful as a treatment agent for septicemia, bacterial infection diseases, and the like.

3 Claims, 11 Drawing Sheets

LPC-API 20 ml/kg treated mice 04 (M24)   Enlarged images of left column
Day 14, hUL 3+

LPC-API 10 ml/kg treated mice 02 (M27)   Enlarged images of left column
Day 14, hUL 1+

LPC-API 5 ml/kg treated mice 04 (M34)   Enlarged images of left column
Day 14, hUL 1+

LIPID NANOMATERIAL CONTAINING LYSOPHOSPHATIDYLCHOLINE OR DERIVATIVE THEREOF AND METHOD FOR PREPARING SAME

TECHNICAL FIELD

The present invention relates to a lipid nanomaterial containing lysophosphatidylcholine or an ether derivative thereof, a method for preparing the same, a method for reducing hemolysis and erythrocyte aggregation using the compound, and a pharmaceutical formulation containing the lipid nanomaterial.

BACKGROUND ART

Lysophosphatidylcholine (LPC), which is a major component of oxidized low-density lipoprotein, is known to have relatively beneficial effects on sepsis by activating various immunocompetent cells including monocytes, phagocytes, and neutrophilic leukocytes. In addition, it is known that the administration of LPC significantly lowers mortality due to peritonitis in peritonitis animal models and cecal ligation and puncture (CLP) animal models, and produces effects on the treatment of various bacterial infection diseases, including peritonitis, pneumonia, osteomyelitis, cellulites, osteomyelitis, and the like, through inherent immunity enhancement (Korean Patent Nos. 10-0842160 and 10-0849448). In addition, it is known that LPC can be used as a therapeutic agent for acute respiratory distress syndromes and multiple organ dysfunction syndromes (Korean Patent No. 10-0842159).

However, due to very low solubility in the aqueous phase, LPC compounds have limits in the development of stable pharmaceutical formulations, for example, the in vivo bioavailability of the LPC compounds is low when they are dissolved in the aqueous phase for preparing medicinal products, such as sterile water, injectable water, deionized water, and buffer solvent and then administered, or the LPC compounds are precipitated in the body fluid and tissues immediately after the in vivo administration even though they are solubilized formulations. Moreover, LPC compounds induce hemolysis and erythrocyte aggregation (Tanaka Y. et al., J Biochem. 94(3):833-40 (1983)), and exhibit remarkable local irritation of LPC itself at the time of subcutaneous administration in animal experiments (Ryborg A K, et al., Acta Derm Venereol. 80(4):242-6 (2000)). Therefore, the development of novel formulations for overcoming such defects is required.

Throughout the entire specification, many papers and patent documents are referenced and their citations are represented. The disclosure of cited papers and patent documents are entirely incorporated by reference into the present specification, and the level of the technical field within which the present invention falls, and details of the present invention are explained more clearly.

DETAILED DESCRIPTION OF THE INVENTION

Technical Problem

The present inventors have searched and endeavored to solve low solubility, local irritation, and hemolysis and erythrocyte aggregation of lysophosphatidylcholine. As a result, the present inventors have formulated lysophosphatidylcholine into a lipid nanomaterial form, and have verified through animal experiments that the lipid nanomaterial formulation does not exhibit local irritation and can significantly reduce hemolysis and erythrocyte aggregation of lysophosphatidylcholine, and then have completed the present invention.

Therefore, an aspect of the present invention is to provide a lipid nanomaterial containing lysophosphatidylcholine or an ether derivative thereof.

Another aspect of the present invention is to provide a method for preparing the lipid nanomaterial.

Still another aspect of the present invention is to provide a method for reducing toxicity of lysophosphatidylcholine or an ether derivative thereof.

Still another aspect of the present invention is to provide a method for reducing hemolysis or erythrocyte aggregation of lysophosphatidylcholine or an ether derivative thereof.

Still another aspect of the present invention is to provide a pharmaceutical formulation for oral or parenteral administration, containing lysophosphatidylcholine or an ether derivative thereof.

Other purposes and advantages of the present disclosure will become more obvious with the following detailed description of the invention, claims, and drawings.

Technical Solution

In accordance with an aspect of the present invention, there is provided a lipid nanomaterial, including: (a) a lipid construct containing a triglyceride, oil, and lecithin; and (b) lysophosphatidylcholine or an ether derivative thereof, as a pharmaceutically active ingredient.

The present inventors have searched and endeavored to solve low solubility, local sensitivity, and hemolysis and erythrocyte aggregation of lysophosphatidylcholine. As a result, the present inventors have formulated lysophosphatidylcholine into a lipid nanomaterial form, and have verified through animal experiments that the lipid nanomaterial formulation does not exhibit local irritation and can significantly reduce hemolysis and erythrocyte aggregation of lysophosphatidylcholine.

As used herein, the term "lipid construct" refers to a nano-sized material (e.g., nanoparticles) prepared by using a lipid mixture containing a triglyceride, oil, and lecithin, and the term "lipid nanomaterial" refers to a nano-sized material including both the lipid construct and lysophosphatidylcholine or a derivative thereof. The form and shape of the lipid nanomaterial are not particularly limited so long as the lipid nanomaterial is a nano-sized material.

According to an embodiment of the present invention, the lipid nanomaterial is lipid nanoparticles. The lipid nanoparticles have a diameter of 1-1000 nm for one particular embodiment, a diameter of 1-500 nm for another particular embodiment, a diameter of 20-200 nm for still another embodiment, and a diameter of 50-200 nm for still another embodiment. The drug encapsulation ratio of the lipid nanoparticles is lowered for the lipid nanoparticles having a size of smaller than 1 nm, and the lipid nanoparticles are difficult to use as an injection for the lipid nanoparticles having a size of larger than 1000 nm.

According to an embodiment of the present invention, the lipid construct (or lipid nanomaterial) of the present invention is emulsion phase nanoparticles.

According to an embodiment of the present invention, regarding components of the lipid construct, the triglyceride and oil are lipid components for forming the structure of the lipid construct (or lipid nanomaterial), and the lecithin is an emulsifier.

According to an embodiment of the present invention, the triglyceride may be a middle chain triglyceride (MCT). The middle chain triglyceride is a $C_6$-$C_{12}$ fatty acid ester compound of glycerol. The middle chain triglyceride usable herein includes Miglyol 812 (caprylic/capric triglyceride), Miglyol 818 (caprylic/capric/linoleic triglyceride), Miglyol 829 (caprylic/capric/succinic triglyceride), and a combination thereof.

According to an embodiment of the present invention, the oil is vegetable oil. The vegetable oil usable herein includes soybean oil, palm oil, rapeseed oil, sunflower seed oil, peanut oil, cottonseed oil, palm kernel oil, coconut oil, poppy seed oil, safflower oil, sesame oil, corn oil, olive oil, canola oil, and a combination thereof.

According to an embodiment of the present invention, the lecithin includes egg lecithin, soybean lecithin, Non-GMO lecithin, rapeseed lecithin, sunflower lecithin, lysolecithin, and a combination thereof.

According to an embodiment of the present invention, the lipid construct may further contain a phospholipid capable of forming a structure of the lipid construct, an ionic lipid capable of preventing lipid constructs from aggregating each other, or a stabilizer capable of stabilizing the structure of the lipid construct.

According to one particular embodiment, the phospholipid that may be added to the lipid construct is an arbitrary phospholipid, or a combination of phospholipids capable of forming a liposome. For example, natural phospholipids obtained from eggs, soy beans, or other vegetable sources, phosphatidylcholine (HPSC) containing semi-synthetic phospholipids or synthetic phospholipids, phospholipids having various lipid chain lengths, and unsaturated phospholipids may be used herein. Specifically, at least one selected from the group consisting of distearoyl phosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoyl phosphatidylcholine (DPPC), dimyristoyl phosphatidylcholine (DMPC), and a combination thereof may be used.

According to a particular embodiment, the ionic lipid that may be added to the lipid construct is anionic lipid or cationic lipid. Examples of the anionic lipid may include dimyristoyl phosphatidylglycerol (DMPG), dilauryl phosphatidylglycerol (DLPG), dipalmitoyl phosphatidylglycerol (DPPG), distearoyl phosphatidylglycerol (DSPG), dimyristoyl phosphatidic acid (DMPA), distearoyl phosphatidylglycerol (DSPA), dilauryl phosphatidic acid (DLPA), dipalmitoyl phosphatidic acid (DPPA), and a combination thereof. In addition, example of the cationic lipid may include dioleoyl trimethylammonium propane (DOTAP), dimethyl octadecyl ammonium (DMOA), dioleoyl phosphatidyl ethanol amine (DOPE), dialkyl dimethyl ammonium bromide (DXDAB), dialkyl trimethyl ammonium propane (DXTAP), and a combination thereof.

According to one particular embodiment, the stabilizer that may be added to the lipid construct is ethylenediaminetetraacetate (EDTA) or a salt thereof (e.g., sodium salt).

According to an embodiment of the present invention, the weight ratio of triglyceride:oil:lecithin in the lipid construct may be 1:0.5-10:1-15. The weight ratio is 1:0.5-3:2-10 for one particular embodiment, and 1:0.5-2:2-5 for another particular embodiment.

The lipid nanomaterial of the present invention contains, as a pharmaceutically active ingredient, lysophosphatidylcholine or an ether derivative thereof. The lysophosphatidylcholine or ether derivative thereof is known to have effects on diseases (disorders), such as sepsis, bacterial infection diseases (e.g., peritonitis or pneumonia), acute respiratory distress syndromes, and multiple organ dysfunction syndromes.

According to an embodiment of the present invention, the lysophosphatidylcholine may be represented by Chemical Formula 1 below:

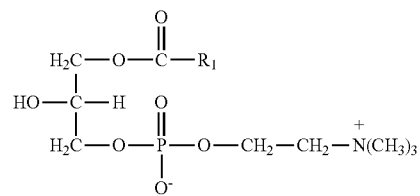

Chemical Formula 1 wherein, $R_1$ is $C_{4-30}$ alkyl, or $C_{4-30}$ alkenyl having one or more double bonds.

According to one particular embodiment, the lysophosphatidylcholine represented by chemical formula 1 is selected from the group consisting of L-α-lysophosphatidylcholine, stearoyl; L-α-lysophosphatidylcholine, myristoyl; L-α-lysophosphatidylcholine, palmitoyl; DL-α-lysophosphatidylcholine, palmitoyl; and L-α-lysophosphatidylcholine, oleoyl.

According to an embodiment of the present invention, the ether derivative of the lysophosphatidylcholine may be represented by Chemical Formula 2 below:

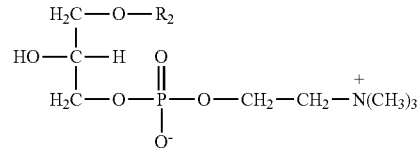

Chemical Formula 2 wherein, $R_2$ is $C_{4-30}$ alkyl, or $C_{4-30}$ alkenyl having one or more double bonds.

According to one particular embodiment, the derivative of lysophosphatidylcholine, represented by chemical formula 2, is selected from the group consisting of L-α-lysophosphatidylcholine, γ-O-alk-1-enyl; L-α-lysophosphatidylcholine, γ-O-alkyl; DL-α-lysophosphatidylcholine, γ-O-hexadecyl; and L-α-lysophosphatidylcholine, γ-O-hexadecyl.

According to an embodiment, the weight ratio of the lysophosphatidylcholine or ether derivative thereof and the lipid construct may be 1:1-50. The weight ratio is 1:1-10 for one particular embodiment, and 1:3-7 for another particular embodiment.

According to an embodiment of the present invention, the lipid nanomaterial has characteristics of (i) the improvement in solubility, (ii) the reduction in toxicity, (iii) the reduction in hemolysis, or (iv) the reduction in erythrocyte aggregation, compared with the lysophosphatidylcholine or the ether derivative thereof.

In accordance with another aspect of the present invention, there is provided a pharmaceutical formulation for oral or parenteral administration, containing: (a) a pharmaceutically effective amount of the lipid nanomaterial of any one of claims 1 to 7; and (b) a pharmaceutically acceptable carrier.

The lipid nanomaterial according to the present invention may be formulated in various oral or parenteral formulations. The oral formulation includes, for example, tablet, pill, soft/hard capsule, liquid, syrup, granule, elixir, and the like. These formulations may be prepared using, in addition to the active ingredient, at least one of pharmaceutically acceptable carriers including diluents or excipients, such as a filler, an extender, a wetting agent, a disintegrant, a lubricant, a binder, and a surfactant, which are generally used in the art. Suitable pharmaceutically acceptable carriers and formulations are described in detail in *Remington's Pharmaceutical Sciences* (19th ed., 1995).

Agar, starch, alginic acid or sodium salt thereof, and anhydrous calcium monohydrogen phosphate may be used as the disintegrant; silica, talc, stearic acid or magnesium salt or calcium salt thereof, and polyethylene glycol may be used as the lubricant; and magnesium aluminum silicate, starch paste, gelatin, tragacanth, methylcellulose, sodium carboxymethylcellulose, polyvinylpyrrolidone, and low-substituted hydroxypropylcellulose may be used as the binder. Besides, lactose, dextrose, sucrose, mannitol, sorbitol, cellulose, or glycine may be used as the diluent, and in some cases, an azeotropic mixture, an absorbent, a colorant, a flavor, a sweetener, and the like, which are generally known in the art, may be used together.

The pharmaceutical formulation according to the present invention may be parenterally administered, and the parenteral administration includes a method of injecting a subcutaneous, intravenous, intramuscular, or intrathoracic injection, or a method for transdermally administering a transdermal preparation. Here, for the formulation into an injection, the lysophosphatidylcholine or ether derivative thereof may be mixed with a stabilizer or a buffer in water to prepare a solution or a suspension, which is then prepared in a unit dosage form of an ampoule or a vial. In addition, for the formulation into a transdermal preparation, the lysophosphatidylcholine or ether derivative thereof may be formulated by being stored in a drug storing layer of a patch, composed of a drug protection layer, the drug storage layer, a release rate control membrane, and an adhesive.

The pharmaceutical formulation may be sterilized, or may contain adjuvants, such as a preservative, a stabilizer, a salt for regulating the osmotic pressure, and a buffer, and other therapeutically useful materials, and may be formulated by a mixing, granulizing, or coating method, which are conventional methods. If necessary, the pharmaceutical formulation of the present invention may be administered in combination with other medicines, for example, other sepsis therapeutic agents.

The pharmaceutical formulation may contain an aqueous solvent (water).

In cases where the pharmaceutical formulation of the present invention is formulated in a unit dosage form, lysophosphatidylcholine or an ether derivative thereof, as an active ingredient, may be contained at a unit dose of about 0.1-1,500 mg. A suitable dose thereof may vary depending on various factors, including the formulation method, manner of administration, patient's age, body weight, gender, and disease severity, diet, time of administration, route of administration, excretion rate, and response sensitivity. The dose required for treatment of an adult is usually in the range of about 1-500 mg per day depending on the frequency and intensity of administration. In the case of intramuscular or intravenous administration into an adult, about 5-300 mg per day may be sufficient as a separate single dose, but a higher dose per day is preferable for some patients.

In addition, the pharmaceutical formulation according to the present invention may contain an antioxidant that is conventionally used, such as ethylenediaminetetraacetic acid, erythorbic acid, dibutyl hydroxy toluene, butyl hydroxy anisole, propyl gallate, α-tocoperol, ρ-tocoperol, γ-tocoperol, and δ-tocoperol. Further, the pharmaceutical formulation according to the present invention may contain a tonicity modifier that is conventionally used, such as sucrose or mannitol.

In accordance with another aspect of the present invention, there is provided a method for preparing a lipid nanomaterial containing lysophosphatidylcholine or an ether derivative thereof, the method including:

(a) obtaining a lipid mixture solution by mixing lysophosphatidylcholine or an ether derivative thereof with an aqueous solvent, a triglyceride, oil, and lecithin;

(b) homogenizing the lipid mixture solution in step (a);

(c) adjusting the homogenized lipid mixture solution in step (b) to pH 3-7; and (d) emulsifying the pH-adjusted lipid mixture solution in step (c) to form a nano-sized lipid nanomaterial.

The descriptions of the overlapping contents between the method for preparing a lipid nanomaterial of the present invention and the foregoing lipid nanomaterial are omitted to avoid excessive complication of the present specification.

In step (a), the lipid mixture solution is obtained by adding a lipid mixture containing a triglyceride, oil, and lecithin, and lysophosphatidylcholine or an ether derivative thereof to an aqueous solvent.

According to an embodiment of the present invention, the weight ratio of the lysophosphatidylcholine or ether derivative thereof: triglyceride:oil:lecithin may be 1:0.5-10:0.5-10:1-15. The weight ratio is 1:0.5-3:0.5-3:2-10 for one particular embodiment, and 1:0.5-2:0.5-2:2-5 for another particular embodiment.

According to an embodiment of the present invention, the concentrations of triglyceride, oil, lecithin, and lysophosphatidylcholine (or ether derivative thereof) in the lipid mixture solution may be 1-100 mg/ml.

According to an embodiment of the present invention, in step (a), the lipid mixture solution may be prepared by adding an antioxidant or a tonicity modifier.

In step (b), the lipid mixture solution is homogenized through the conventional homogenization method.

According to an embodiment of the present invention, the homogenization may be conducted using a homogenizer at 2,000-10,000 rpm (e.g., 3,000-7,000 rpm). The time for homogenization is not particularly limited, and thus the homogenization may be conducted for 2-4 hours, and the homogenization procedure may be repeatedly conducted twice or more.

In step (c), an acid or a base is added to the homogenized lipid mixture solution, such that the solution is adjusted to pH 3-7. The pH adjustment as above is advantageous in the pharmaceutical use and stability of the lipid nanomaterial.

According to an embodiment of the present invention, in step (c), the lipid mixture solution may be adjusted to pH 4-6.

Herein, the pH-adjusted lipid mixture solution may be further homogenized.

In step (d), the pH-adjusted lipid mixture solution is emulsified to form a nano-sized lipid nanomaterial. The emulsification may be conducted using a microfluidic system or an encapsulator.

According to an embodiment of the present invention, the finally prepared lipid nanomaterial is a semi-transparent emulsion.

According to an embodiment of the present invention, in step (d), filter-sterilization may be further conducted using a membrane having a pore size of 0.1-0.5 μm, as needed. If the pore size of the membrane is smaller than 0.1 μm, some of the lipid nanomaterial cannot pass through the membrane, and if the pore size of the membrane is larger than 0.5 μm, some of the nanomaterial may not have a suitable size for an injection.

In accordance with still another aspect of the present invention, there is provided a method for reducing toxicity of lysophosphatidylcholine or an ether derivative thereof, the method including steps (a) to (d) above.

In accordance with still another aspect of the present invention, there is provided a method for reducing hemolysis or erythrocyte aggregation of lysophosphatidylcholine or an ether derivative thereof, the method including steps (a) to (d) above.

In accordance with still another aspect of the present invention, there is provided a method for improving solubility of lysophosphatidylcholine or an ether derivative thereof, the method including steps (a) to (d) above.

As verified in the following examples, the lipid nanomaterial of the present invention has effects of reducing toxicity, hemolysis, and erythrocyte aggregation problems of lysophosphatidylcholine (or ether derivative thereof). Therefore, the lysophosphatidylcholine or ether derivative thereof is formulated into the lipid nanomaterial through steps (a) to (d), so the stability of the compound can be improved, and thus the medicinal use of the compound can be promoted.

Advantageous Effects

Features and advantages of the present invention are summarized as follows.

(i) The present invention is directed to a lipid nanomaterial containing lysophosphatidylcholine or an ether derivative thereof, a method for preparing the same, and a use thereof.

(ii) The lipid nanomaterial of the present invention exhibits significantly improved characteristics in solubility, toxicity, hemolysis, and erythrocyte aggregation, when compared with lysophosphatidylcholine or an ether derivative thereof.

(iii) Thus, the present invention can be favorably used as a therapeutic agent for sepsis, bacterial infection disease, and the like, containing, as an active ingredient, lysophosphatidylcholine or an ether derivative thereof.

EP: epitherlium, ED: epidermis, DM: dermis, HL: hair follicle, CM: cutaneous trunci muscle, scale bars: 160 μm.

Figure 6A:
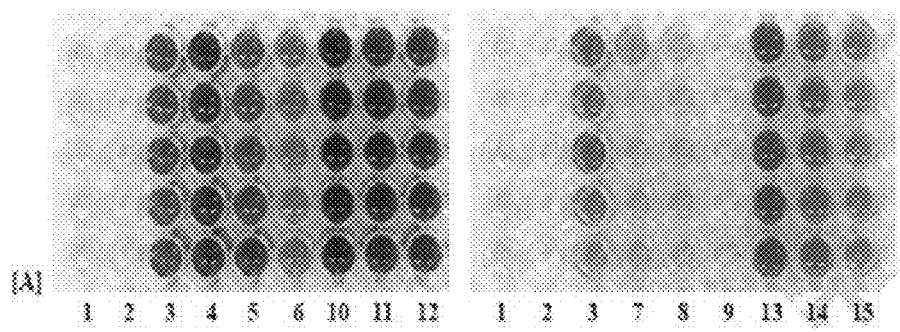
Figure 6A:
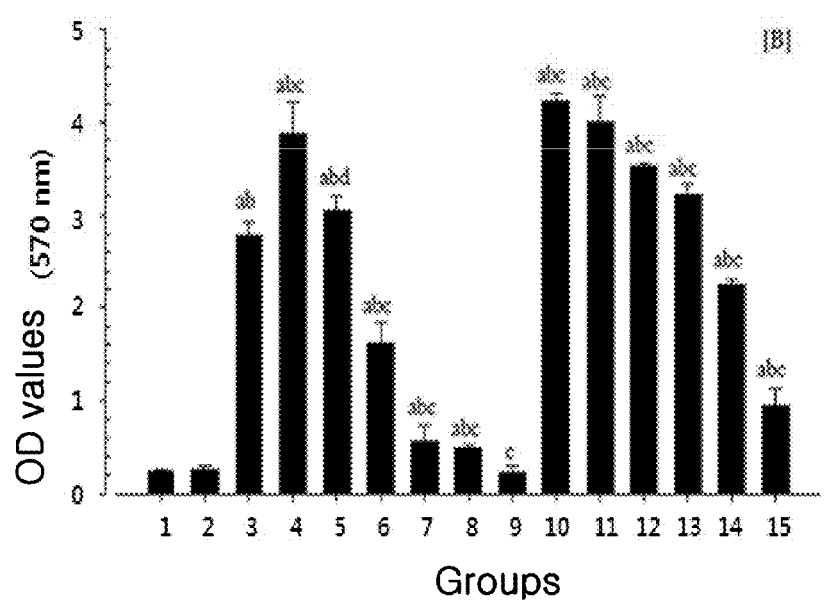
Figure 6B:
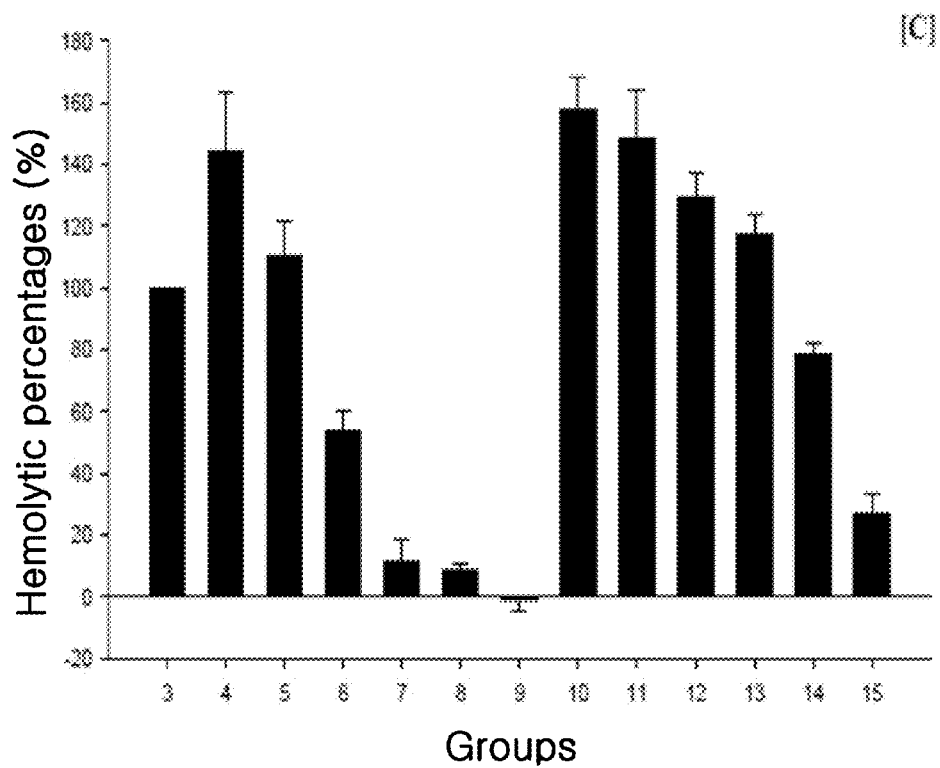

FIGS. 6a and 6b show effects on hemolysis by LPC saline suspension (LPC-API) or LPC lipid nanomaterial formulation (LPC-F).

Groups: 1=non-treated control, 2=negative saline treated group, 3=positive distilled water treated group, 4=LPC-IV formulation stock, 5=LPC-IV formulation 2-fold dilution, 6=LPC-IV formulation 4-fold dilution, 7=LPC-IV formulation 8-fold dilution, 8=LPC-IV formulation 16-fold dilution, 9=LPC-IV formulation 32-fold dilution, 10=LPC-API saline suspension stock, 11=LPC-API saline suspension 2-fold dilution, 12=LPC-API saline suspension 4-fold dilution, 13=LPC-API saline suspension 8-fold dilution, 14=LPC-API saline suspension 16-fold dilution, 15=LPC-API saline suspension 32-fold dilution.

a=$p<0.01$ as compared with non-treated control by MW test, b=$p<0.01$ as compared with non-treated negative control by MW test, c=$p<0.01$ as compared with positive control by MW test, d=$p<0.05$ as compared with positive control by MW test.

Figure 7A:
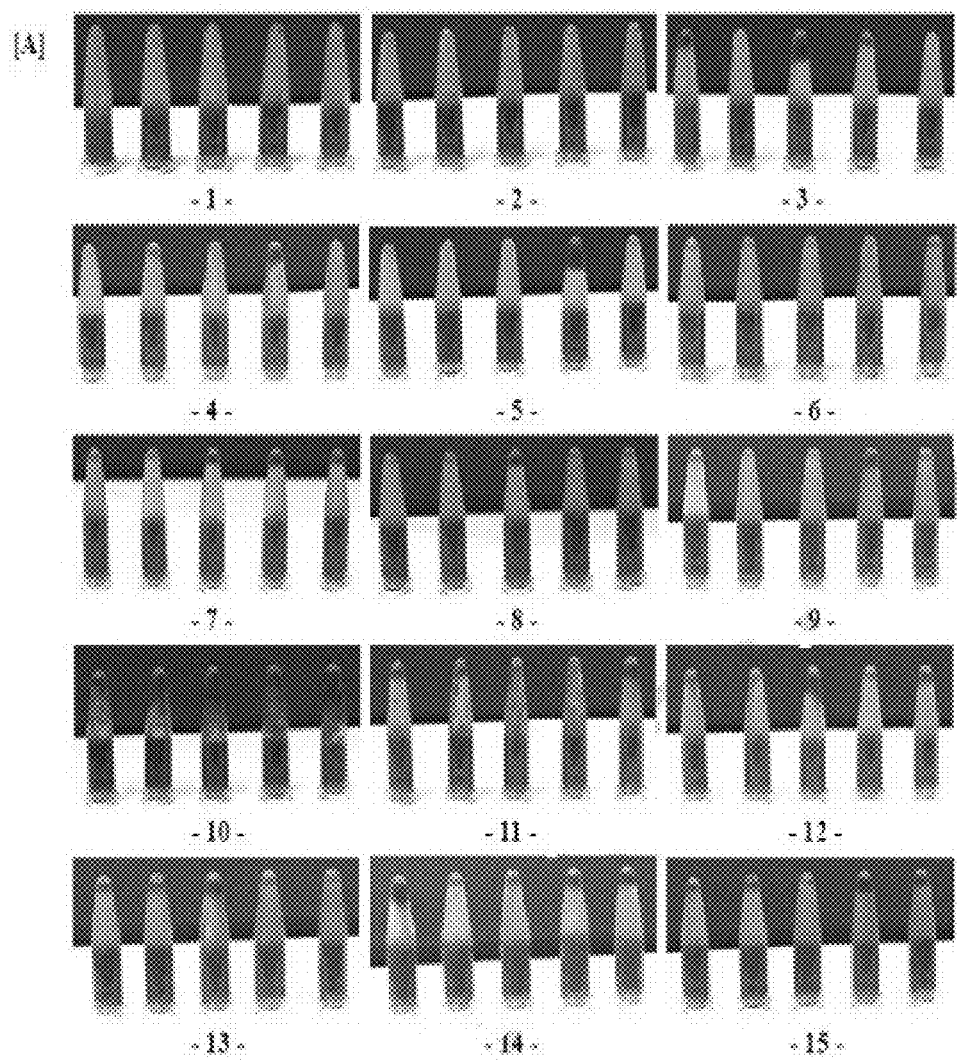
Figure 7B:
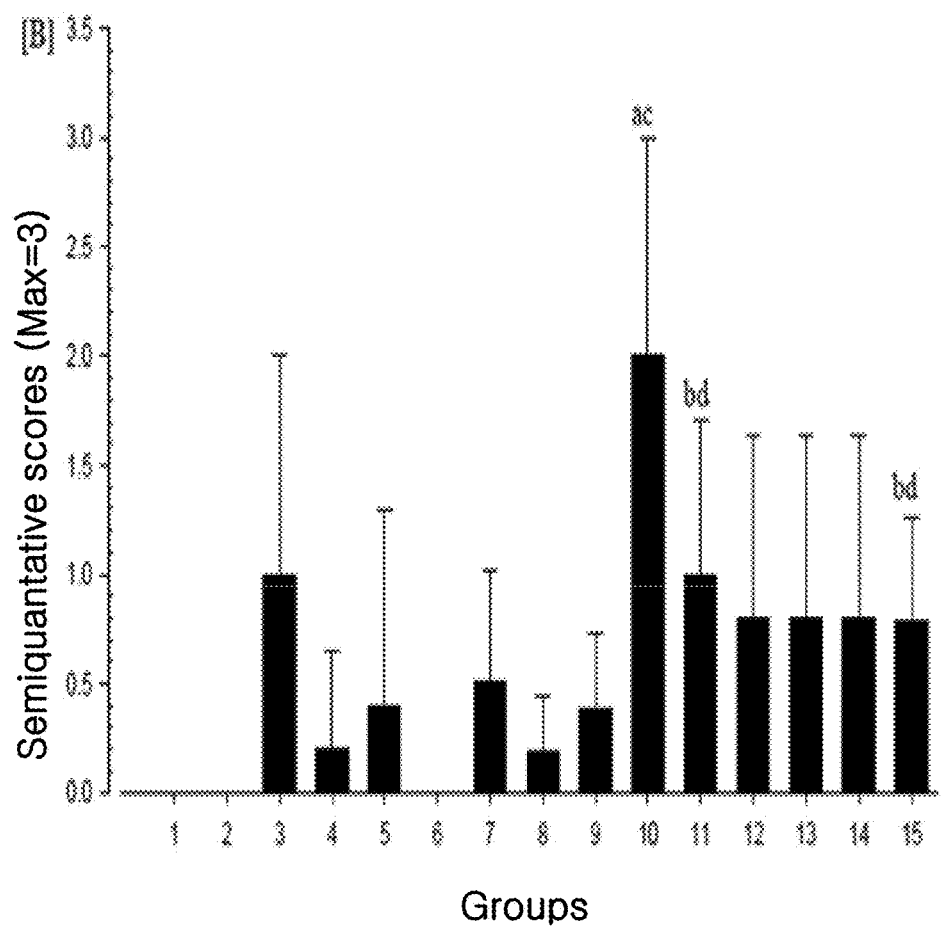

FIGS. 7a and 7b show effects on erythrocyte aggregation by LPC saline suspension (LPC-API) or LPC lipid nanomaterial formulation (LPC-F).

Groups: 1=non-treated control, 2=negative saline treated group, 3=positive distilled water treated group, 4=LPC-IV formulation stock, 5=LPC-IV formulation 2-fold dilution, 6=LPC-IV formulation 4-fold dilution, 7=LPC-IV formulation 8-fold dilution, 8=LPC-IV formulation 16-fold dilution, 9=LPC-IV formulation 32-fold dilution, 10=LPC-API saline suspension stock, 11=LPC-API saline suspension 2-fold dilution, 12=LPC-API saline suspension 4-fold dilution, 13=LPC-API saline suspension 8-fold dilution, 14=LPC-API saline suspension 16-fold dilution, 15=LPC-API saline suspension 32-fold dilution.

a=$p<0.01$ as compared with non-treated control by MW test, b=$p<0.05$ as compared with non-treated control by MW test, c=$p<0.01$ as compared with negative non-treated control by MW test, d=$p<0.05$ as compared with negative non-treated control by MW test.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Preparation of LPC-Containing Lipid Nanomaterial

To lysophosphatidylcholine (LPC 18:0, NOF) 5.00 g, egg lecithin (Lipoid E-80) 15.00 g, soy bean oil 5.00 g, sucrose 50.00 g, EDTA$_2$Na$_2$H$_2$O 27.5 mg, and middle chain triglyceride (Miglyol 812) 5.00 g was added purified water, to make a total weight of 500 g. The mixture solution was homogenized using a homogenizer (L5M-A, Silverson) at 5000 rpm for 3 hours while the temperature was maintained at 20-25° C. The above processes were conducted twice, and then the homogenized solution 1,000 g was adjusted to pH 5.5 using a 0.1 N sodium hydroxide solution or a 0.1 N hydrochloric acid solution. After the pH adjustment, the mixture solution was homogenized for another 30 minutes, and then again adjusted to pH 5.5. The pH-adjusted solution was stored under refrigeration at 10° C. or lower. The above processes were repeated eight times to prepare 8,000 g of a solution which was adjusted to pH 5.5.

The lipid mixture solution containing the lysophosphatidylcholine compound was homogenized and emulsified using a microfluidizer (M-110EH-30, MFIC Corp.) at a pressure of 25,000 psi. This homogenization process was repeated five times, followed by filtration using a 0.2-μm membrane, thereby preparing liquid-phase lipid nanoparticles containing the lysophosphatidylcholine compound.

Example 2: Size Measurement of LPC-Containing Lipid Nanomaterial

The size of the lipid nanoparticles in example 1 was measured using a particle analyzer (ELS-Z2, Otsuka). The measurement results are shown in table 1 and FIG. 1.

TABLE 1

| | Disperson method | Particle size (nm) |
|---|---|---|
| Example 1 | Water is added to lipid mixture solution for dispersion | 87.2 |

Example 3: Calculation of LPC Concentration

Figure 1:
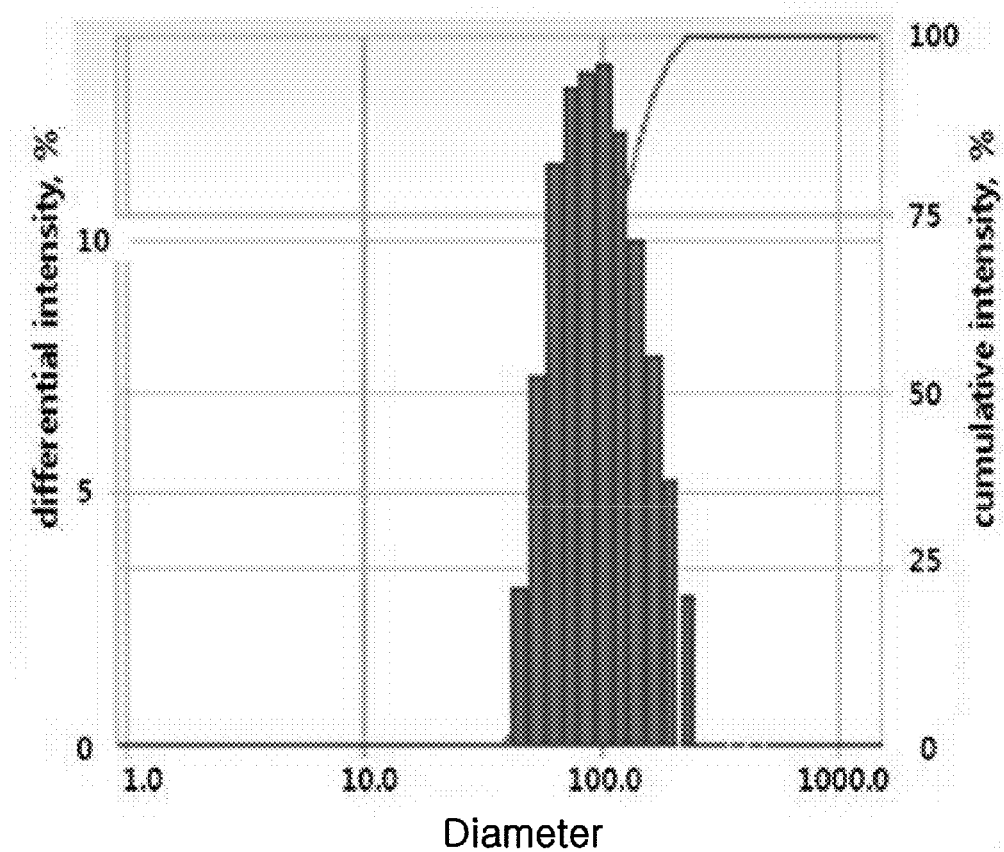
FIG. 1 shows sizes of lipid nanomaterial particles prepared in example 1.

The concentration of the lysophosphatidylcholine compound in the lipid nanoparticle-containing formulation, prepared in example 1, was calculated by comparing the area ratio of the lysophosphatidylcholine compound, which was analyzed in quantitative HPLC-ELSD using 18:0 LPC standard solution, with the area ratio in the standard curve shown in FIG. 1.

Example 4: Evaluation on Stability of LPC-Containing Lipid Nanomaterial

The stability of the lipid nanoparticles prepared in example 1 was evaluated while the lipid nanoparticles were frozen, refrigerated, kept at room temperature, and warmed. The evaluation results are shown in table 2.

TABLE 2

| | Storage conditions | Morphology | Purity (HPLC area %) | Particle size (nm) | pH |
|---|---|---|---|---|---|
| Date of preparation | | Lightly ivory and Semi-transparent | 98 | 79 | 5.13 |
| One month later | −20° C. | Good | 102 | 84 | 5.52 |
| | 2-8° C. | Good | 100 | 77 | 5.42 |
| | 25° C. | Good | 100 | 77 | 5.28 |
| | 30° C. | Good | 99 | 101 | 5.13 |

As shown in table 2, the liquid-phase lipid nanoparticles exhibited stability in the morphology, purity, particle size, and pH even after they were frozen, refrigerated, kept at room temperature, and warmed (30° C.) for one month.

Example 5: Local Irritation Test of LPC-Containing Lipid Nanomaterial Formulation in Mice after Subcutaneous Administration 5-1. Methods In order to evaluate the local irritation of the LPC-containing lipid nanoparticle formulation (LPC-F; 18:0 LPC concentration: 10 mg/ml) prepared in example 1, 20, 10, and 5 ml/kg (18:0 LPC 200, 100, and 50 mg/kg) were single subcutaneously administered to hair-clipped dorsal back skins of mice. Based on the "Testing Guidelines for Safety Evaluation of Drugs" [2009] in Notification No. 2009-116 issued by the Korea Food and Drug Administration, the changes in mortality, body weight, clinical signs, gross and histopathological findings around injection sites during 14 days were compared between the LPC-containing lipid nanoparticle formulations and equal concentrations of lysophosphatidylcholine saline suspension (LPC-API) 10 mg/ml treated group. In the present test, saline was used as negative control, and the highest dosage 200 mg/kg was set based on the maximum permissible dosage 20 ml/kg in rodents (Flecknell, 1996; KFDA Guidelines, Notification 2009-116, 2009; OECD Guidelines, #423, 2001). The dosages were set to 10 and 5 ml/kg in middle and lowest dosage groups, respectively.

Animal male ICR mice were 6-wk old upon receipt (body weight ranged in 30-32 g), and were 10-wk old after acclimatization for 28 days (body weight ranged in 36.4-49.0 g). The animals were distributed into the following groups for the test.

TABLE 3

| Group | Sex | Dose (mg/kg LPC dose) | Animal No. |
|---|---|---|---|
| Negative control | Male | Saline 20 ml/kg | M01-M05 |
| Active | Male | LPC-F 20 ml/kg (200 mg/kg) | M06-M10 |
| Active | Male | LPC-F 10 ml/kg (100 mg/kg) | M11-M15 |
| Active | Male | LPC-F 5 ml/kg (50 mg/kg) | M16-M20 |
| Reference | Male | LPC-API 20 ml/kg (200 mg/kg) | M21-M25 |
| Reference | Male | LPC-API 10 ml/kg (100 mg/kg) | M26-M30 |
| Reference | Male | LPC-API 5 ml/kg (50 mg/kg) | M31-M35 |

All data were expressed as mean±standard deviation (SD) of five mice. Multiple comparison tests for different dosage groups were conducted. Variance homogeneity was examined using the Levene test (Levene A, *Clin Otalary,* 1981; 6:145-51). If the Levene test indicated no significant deviations from variance homogeneity, the obtained data were analyzed by one-way ANOVA followed by Scheffe test to determine which pairs of group comparison were significantly different. In cases where significant deviations from variance homogeneity were observed at Levene test, the non-parametric comparison test and Kruskal-Wallis H test were conducted. In cases where a significant difference was observed in the Kruskal-Wallis H test, the Mann-Whitney U (MW) test was conducted to determine the specific pairs of group comparison, which are significantly different. Statistical analyses were conducted using SPSS (Release 14.0 K, SPSS Inc., USA; Ludbrook, *Clin Exp Pharmacol Physiol,* 1997; 24:294-6). A p-value <0.05 was considered statistically significant.

5-2. Results

<Mortalities>

No mortalities related to LPC-F administration were detected throughout 14 days of observation period.

<Clinical Signs>

Figure 3:
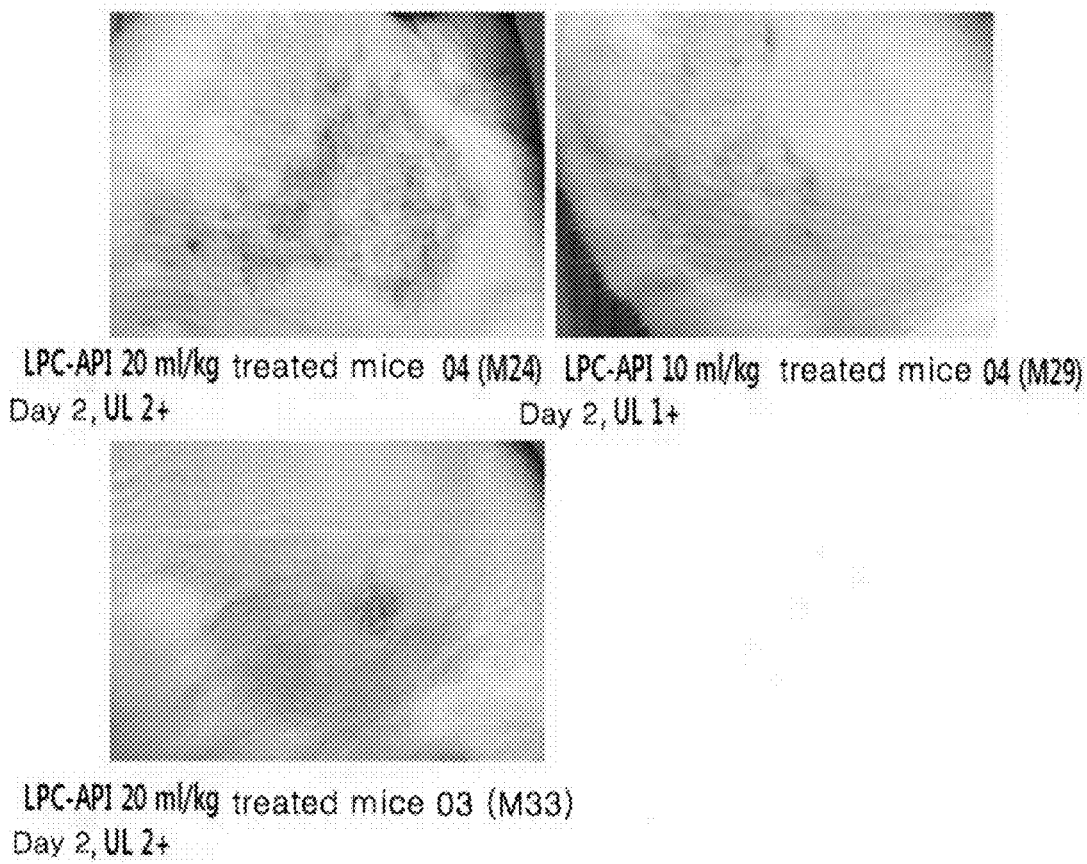
FIG. 3 shows mice skin images illustrating local irritation (toxicity) of LPC.

No meaningful clinical signs were detected in negative saline treated vehicle control and all three different dosages of LPC-F treated groups. However, slight [1+] or moderate [2+] ulcerative skin lesions around injection sites were demonstrated in LPC-API 200, 100, 50 mg/kg treated groups from 48 hrs after end of treatment. Various [1−3+] degrees of ulcerative skin lesions around injection sites were noticed in 5 (5/5; 100%), 3 (3/5; 60%) and 3 (3/5; 60%) mice of LPC-API 200, 100, and 50 mg/kg treated groups from 3 days after treatment, respectively (Table 4 and FIG. 3).

TABLE 4

| Groups | Clinical signs | |
|---|---|---|
| | Normal appearance | Skin ulcerative lessions |
| Vehicle control | | |
| Salin 20 ml/kg | 5/5 (100%) | 0/5 (0%) |
| LPC-F | | |
| 20 ml/kg | 5/5 (100%) | 0/5 (0%) |
| 10 ml/kg | 5/5 (100%) | 0/5 (0%) |
| 5 ml/kg | 5/5 (100%) | 0/5 (0%) |
| LPC-API | | |
| 20 ml/kg | 0/5 (0%) | 5/5 (100%) |
| 10 ml/kg | 2/5 (40%) | 3/5 (60%) |
| 5 ml/kg | 2/5 (40%) | 3/5 (60%) |

<Necropsy Findings>

Figure 4A:
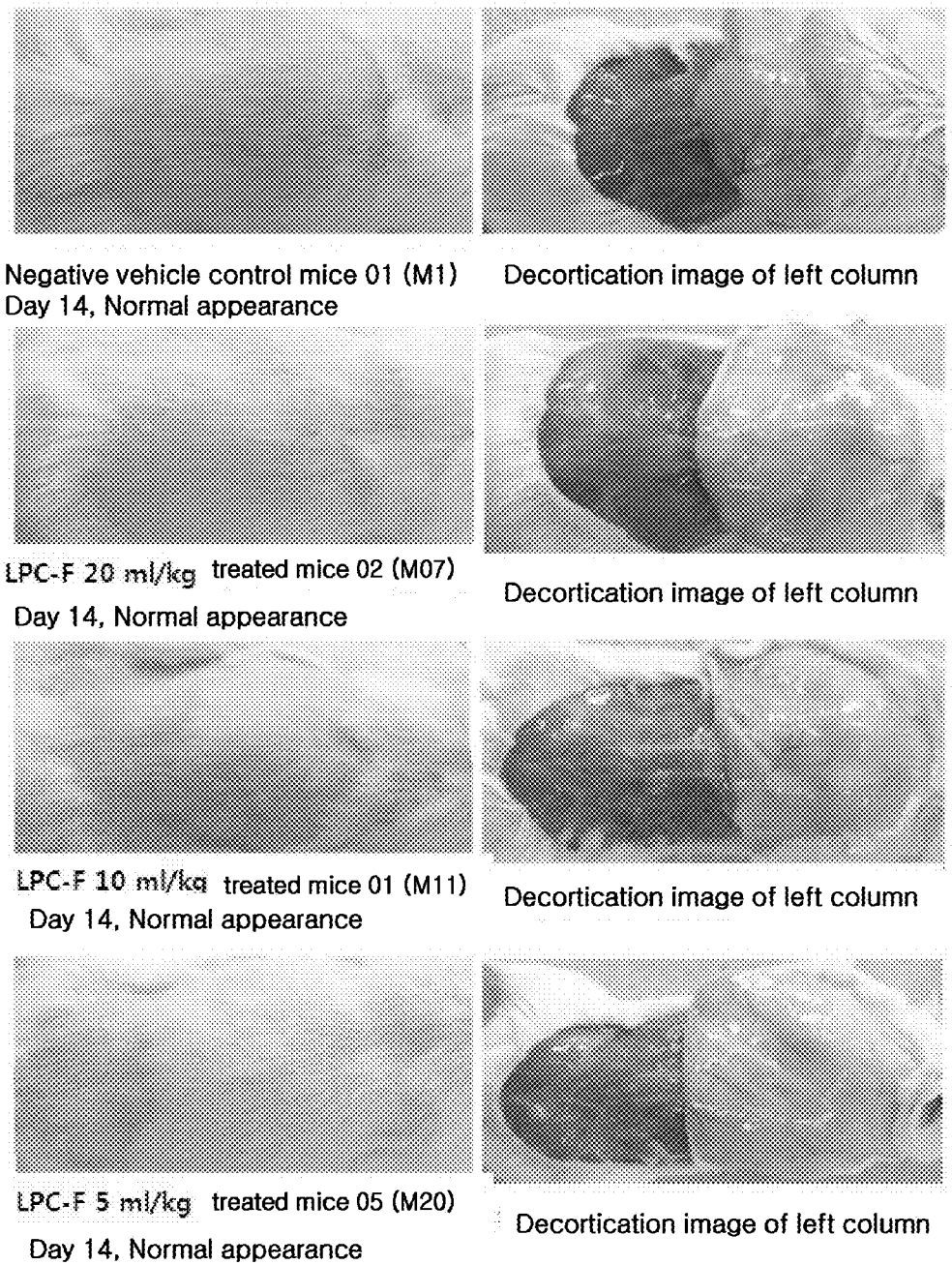
FIGS. 4a and 4b show mouse images illustrating local irritation (toxicity) according to LPC-F or LPC-API administration.
Figure 4B:
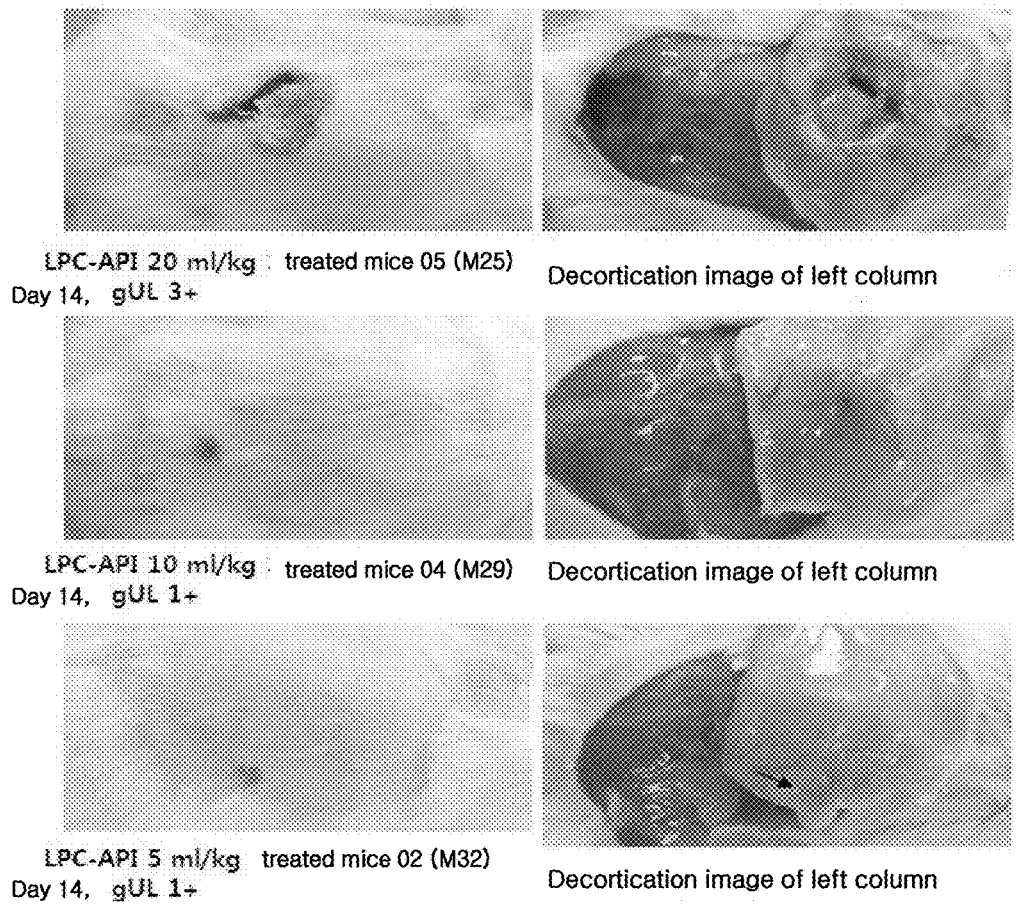
Figure 5A:
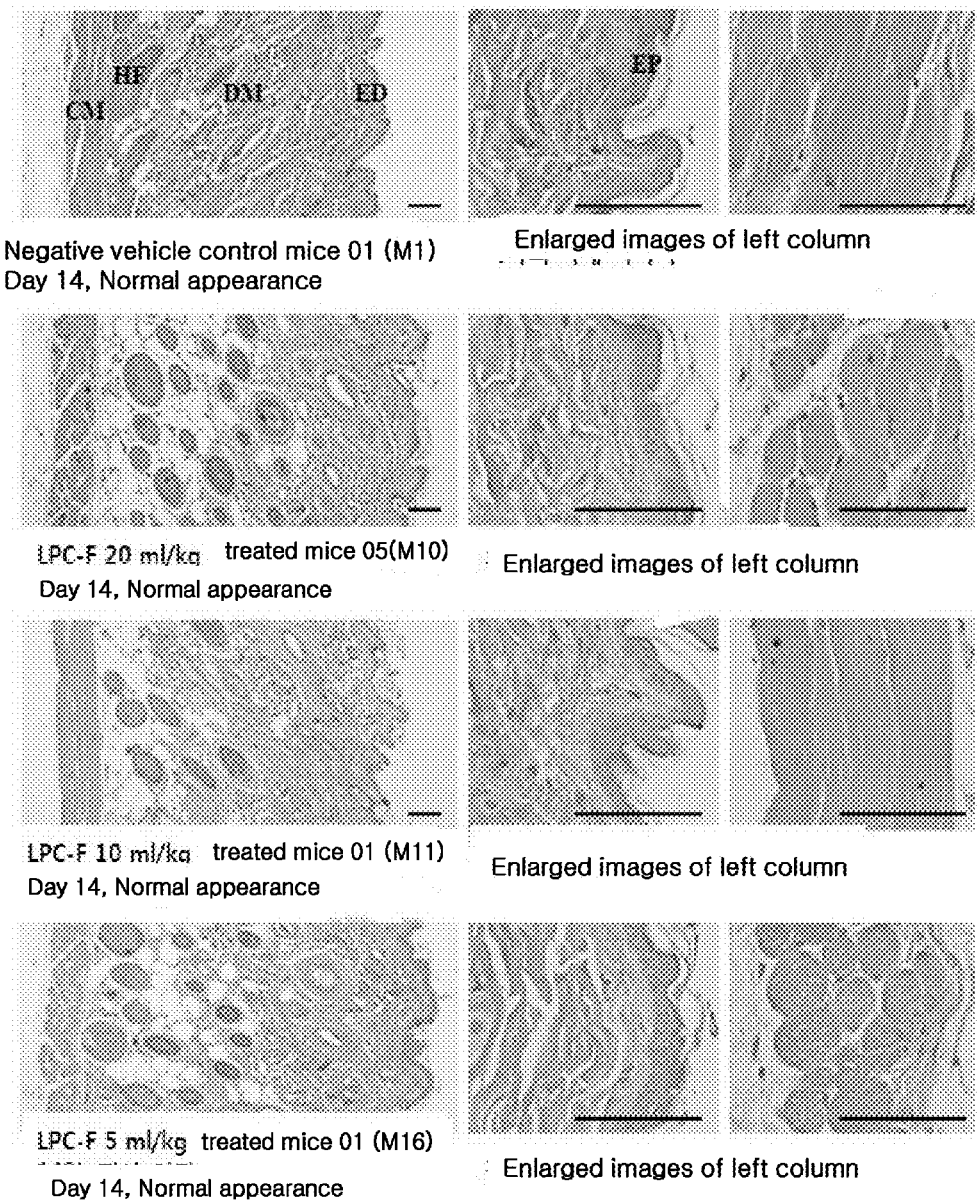
FIGS. 5a and 5b show histopathological results illustrating local irritation (toxicity) according to LPC-F or LPC-API administration.
Figure 5B:
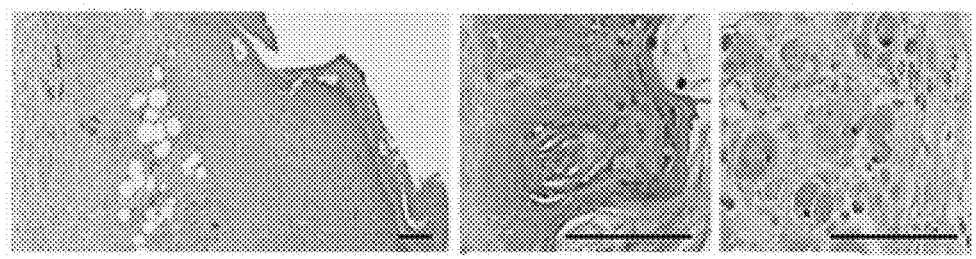
Figure 5B:
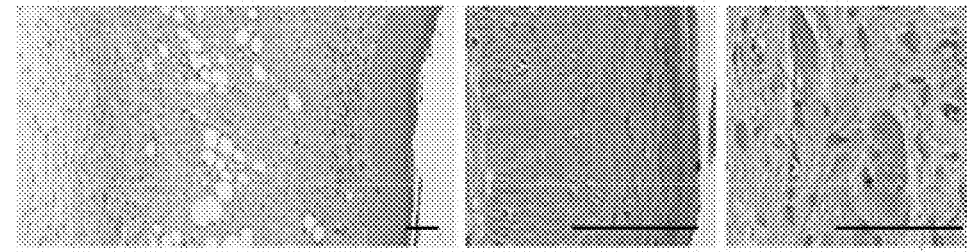
Figure 5B:
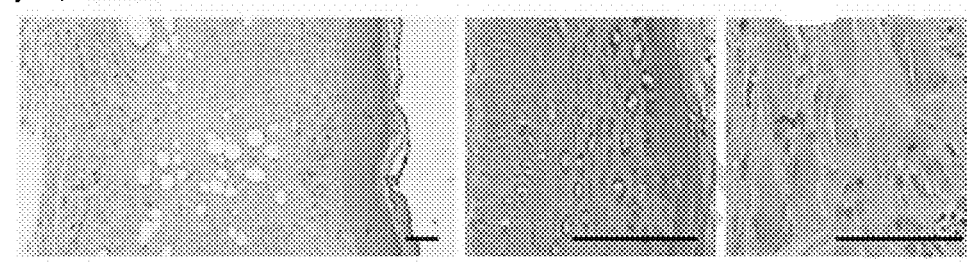

No meaningful gross findings around injection sites were noticed in negative saline treated vehicle control and all three different dosages of LPC-F treated groups. However, various degrees [1-3+] of skin ulcerative lesions around injection sites were noticed in 5 (5/5; 100%), 3 (3/5; 60%), and 3 (3/5; 60%) mice of LPC-API 200, 100, and 50 mg/kg treated groups, respectively (Table 5 and FIG. 4).

TABLE 5

| | Groups | | | | | | |
|---|---|---|---|---|---|---|---|
| | Vehicle control Saline | LPC-F | | | LPC-API | | |
| Skins[a] | 20 ml/kg | 20 ml/kg | 10 ml/kg | 5 ml/kg | 20 ml/kg | 10 ml/kg | 5 ml/kg |
| Normal | 5/5 | 5/5 | 5/5 | 5/5 | 0/5 | 2/5 | 2/5 |
| gUL[b] | 0/5 | 0/5 | 0/5 | 0/5 | 5/5 | 3/5 | 3/5 |
| 1+ | 0/5 | 0/5 | 0/5 | 0/5 | 3/5 | 3/5 | 3/5 |
| 2+ | 0/5 | 0/5 | 0/5 | 0/5 | 1/5 | 0/5 | 0/5 |
| 3+ | 0/5 | 0/5 | 0/5 | 0/5 | 1/5 | 0/5 | 0/5 |

[a]Skins around injectin sites
[b]gUL = Gross skin ulcerative lesions - focal desquamation of full skins, formation of focal creaters with scab formations around injection sites (FIG. 4)
Degree = 1+, Slight; 2+, Moderate; 3+, Severe <Histopathological Findings>

No meaningful skin histopathological findings were detected in negative saline treated vehicle control and all three different dosages of LPC-F treated groups. However, various degrees [1~3+] of skin ulcerative lesions, focal desquamation of epidermis to dermis, hyperplasia of epithelial cells, coarse connective tissues in dermis, inflammatory cell infiltration, and lysis of cutaneous trunci muscles were detected in 5 (5/5; 100%), 3 (3/5; 60%), and 3 (3/5; 60%) mice of LPC-API 200, 100, and 50 mg/kg treated groups, respectively (Table 6 and FIG. 5).

TABLE 6

| | Groups | | | | | | |
|---|---|---|---|---|---|---|---|
| | Vehicle control Saline | LPC-F | | | LPC-API | | |
| Skins[a] | 20 ml/kg | 20 ml/kg | 10 ml/kg | 5 ml/kg | 20 ml/kg | 10 ml/kg | 5 ml/kg |
| Normal | 5/5 | 5/5 | 5/5 | 5/5 | 0/5 | 2/5 | 2/5 |
| hUL[b] | 0/5 | 0/5 | 0/5 | 0/5 | 5/5 | 3/5 | 3/5 |
| 1+ | 0/5 | 0/5 | 0/5 | 0/5 | 3/5 | 3/5 | 3/5 |
| 2+ | 0/5 | 0/5 | 0/5 | 0/5 | 1/5 | 0/5 | 0/5 |
| 3+ | 0/5 | 0/5 | 0/5 | 0/5 | 1/5 | 0/5 | 0/5 |

[a]Skins around injection sites
[b]hUL = hispatholoigical skin ulcerative lesions - focal desquamation of epidermis to dermis, hyperplasia of epithelial cells, coarse connective tissues in dermis, inflammatory cell infiltration and lysis of cutaneous trunci muscles (FIG. 5)
Degree = 1+, Slight; 2+, Moderate; 3+, Severe <Conclusion>

Gross and histopathological changes around injection sites, detected after the subcutaneous treatment of test materials, provided rapid and reliable evidences on the local irritation of the subcutaneously injected materials, based on which the local irritations of various materials have been evaluated (Gunzel V P, et al., Arzneimittelforschung. 26:1476-9 (1976); Limberger and Lenz, Dtsch Stomatol. 41:407-10 (1991); Reuling et al., Dtsch Zahnarztl Z. 46:694-81991 (1991)). As the results of the present test, the single subcutaneous treatment of LPC-API induced severe skin ulcerative lesions around injection sites, but no meaningful skin findings around injection sites were detected in LPC-F treated groups compared with negative vehicle control.

These results show that the local irritation of LPC itself was remarkably reduced by the lipid nanoparticle formulations of the present invention.

Example 6: Evaluation on Hemolysis and Erythrocyte Aggregation of LPC-Containing Lipid Nanomaterial Formulation 6-1. Methods In order to evaluate the degree of hemolysis and erythrocyte aggregation induced by LPC-containing lipid nanoparticles (LPC-F; 18:0 LPC concentration: 10 mg/ml) prepared in example 1, 200 μl of saline, distilled water, six different concentration solutions (stock, 2, 4, 8, 16 and 32-fold diluted solutions) of LPC-F, or non-formulated lysophosphatidylcholine (LPC-API) 10 mg/ml concentrated saline solution were directly added into 1 ml of collected heparinized rat (SD rat) bloods, and then, incubated at 37° C. in shaking incubator at 100 rpm for 3 hrs. The prepared LPC-F was fold-diluted with saline to prepare six different concentrations of LPC-F. LPC-API 10 mg/ml concentrated solution was prepared through dispersion in saline, and then fold-diluted with saline to prepare six different concentrations of LPC-API Five independent experiments were repeatedly conducted. If possible, blood taken from same rats was used in each independent experiment. After the incubation in shaking incubator at 100 rpm, the formed erythrocyte aggregation was semi-quantitatively evaluated, and the OD values were calculated for the supernatant in each tube, which was prepared by centrifuging the incubated samples at 12,500 rpm for 10 minutes, and then reading the OD at 570 nm, respectively. Hemolysis was calculated by equation 1 below. The hemolytic reaction was considered positive if the hemolytic percentage was greater than 5%.

Hemolytic percentage (%)=(OD sample−OD negative/(OD positive−OD negative)×100 [Equation 1]

Where negative=saline, and positive=distilled water

Erythrocyte aggregation was evaluated based on semiquantative scores as follows:

Semiquantative erythrocyte aggregation scores (Max=3) 0=not aggregated; 1=slight aggregation; 2 moderate aggregation; 3=severe aggregation OD values and semiquantative erythrocyte aggregation scores were expressed by mean±standard deviation of five independent experiments. Multiple comparison tests for different dose groups were conducted. Variance homogeneity was examined using the Levene test (Levene A, *Clin Otalary*, 1981; 6:145-51). If the Levene test indicated no significant deviations from variance homogeneity, the obtained data were analyzed by one-way ANOVA, followed by the least significant differences (LSD) multiple comparisons test to determine which group pairs differed significantly. In cases where significant deviations from variance homogeneity were observed at Levene test, the non-parametric comparison test and Kruskal-Wallis H test were conducted. When a significant difference was observed in the Kruskal-Wallis H test, the Mann-Whitney U (MW) test was conducted to determine the specific pairs of group comparision, which are significantly different. Statistical analyses were conducted using SPSS (Release 14.0 K, SPSS Inc., USA; Ludbrook, *Clin Exp Pharmacol Physiol*, 1997; 24:294-6). A p-value $p<0.05$ was considered statistically significant.

6-2. Results

<Change in Hemolytic Percentage>

Figure 2:
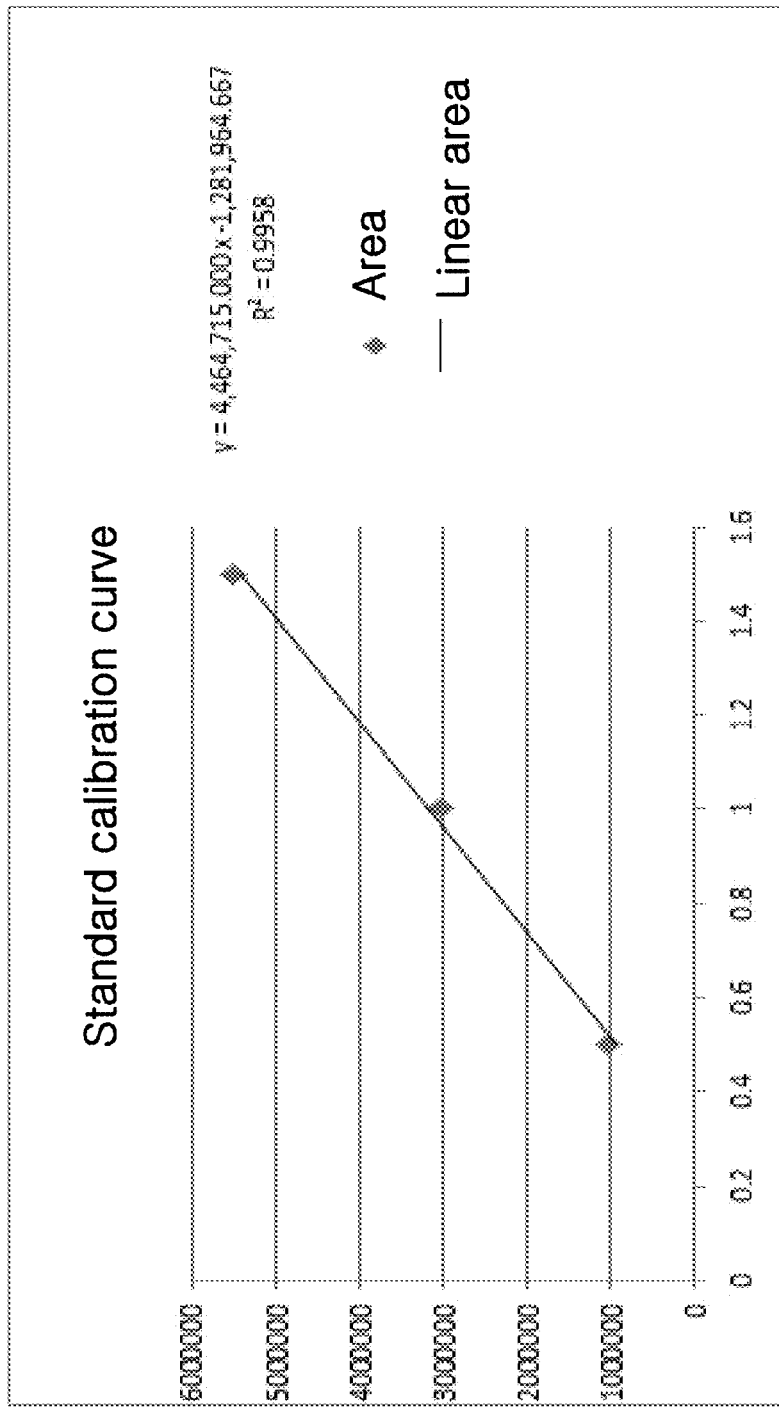
FIG. 2 shows a standard calibration curve for calculating LPC concentration.

Significant ($p<0.01$) decreases of OD values were noticed in LPC-F 4, 8, 16, and 32-fold diluted solutions and LPC-API saline suspension 16 and 32-fold diluted solutions as compared with positive distilled water treated control, respectively. Consequently, the hemolytic percentages (%) were detected as 144.28±18.82, 110.66±11.23, 53.70±6.57, 11.60±6.92, 8.65±2.38, and −1.54±3.16% in LPC-F stock 2, 4, 8, 16, and 32-fold diluted solutions, respectively, and were detected as 157.68±10.44, 148.65±15.01, 129.70±7.23, 117.67±5.97, 78.74±3.30, and 26.86±6.40% in LPC-API saline suspension stock, 2, 4, 8, 16, and 32-fold dilute solutions, respectively (FIG. 2).

The increases of OD values mean the exposure of hemoglobin of plasma, resulting from hemolysis (Kang C, et al., *Comp Biochem Physiol C Toxicol Pharmacol*. 150:85-90 (2009); Zaporowska H, et al., *Folia Histochem Cytobiol*. 34:99-100 (1996)). The results of the present test verified that the hemolytic effects of LPC were markedly decreased by the lipid nanoparticle formulations of the present invention since because no significant increase of OD values and less than 5% hemolytic percentages were detected in LPC-F 32-fold diluted solution, and lower hemolytic effects were observed in LPC-F 4-fold diluted solutions as compared with positive distilled water treated control. On the other hand, LPC-API saline suspension treated groups showed marked increases of OD values, and greater than 5% hemolytic percentages were detected throughout all different concentrations including the lowest 32-fold diluted solutions. Significant increased OD values were detected in stock, 2, 4 and 8-fold diluted LPC-API saline suspension treated groups as compared with positive distilled water treated control.

These results indicated that the hemolytic reaction of LPC could be markedly improved by the lipid nanomaterial formulations of the present invention.

<Evaluation on Erythrocyte Aggregation>

Significant ($p<0.01$ or $p<0.05$) increases of erythrocyte aggregation scores were detected in LPC-API saline suspension stock, 2 and 32-fold diluted solutions as compared with non-treated and negative saline controls. However, significant increases of erythrocyte aggregation scores were detected in all six different concentrations of LPC-API saline suspension treated groups including lowest 32-fold diluted solutions. However, all the LPC-F treated groups of the present invention showed markedly lower erythrocyte aggregation scores as compared with positive distilled water treated control, and no obvious increases of erythrocyte aggregation scores as compared with non-treated or negative controls (FIG. 7).

The increases of erythrocyte aggregations induce various circulatory disorders and irritations, and thus directly related to potential toxicities of test materials (Michel and Seipp, *Arzneimittelforschung*. 40:817-22 (1990); Prasanthi K, et al., *Toxicol In Vitro*. 19:449-56 (2005)). As a result of the present test, LPC, even including lowest 32-fold diluted solutions, induced marked increases of erythrocyte aggregation scores, but no obvious increases in erythrocyte aggregation scores were detected in all the lipid nanoparticle formulation of the present invention including the stock solutions.

These results indicated that the erythrocyte aggregations of LPC were settled by the lipid nanomaterial formulations of the present invention.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A lipid nanomaterial, consisting of:
   (a) a lipid construct consisting of a middle chain triglyceride, oil, and lecithin; and
   (b) lysophosphatidylcholine or an ether derivative thereof, as a pharmaceutically active ingredient,
   wherein the weight ratio of triglyceride: oil: lecithin is 1:0.5-3:2-10, and
   wherein the weight ratio of the lysophosphatidylcholine or ether derivative thereof and the lipid construct is 1:3-7.

2. The lipid nanomaterial of claim 1, wherein the lysophosphatidylcholine is represented by Chemical Formula 1 below, and the ether derivative is represented by Chemical Formula 2:

Chemical Formula 1

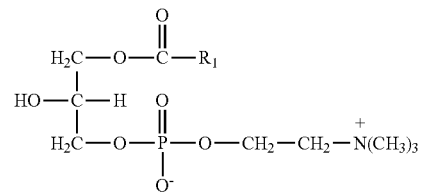

wherein, $R_1$ is $C_{4-30}$ alkyl, or $C_{4-30}$ alkenyl having one or more double bonds, and
Chemical Formula 2
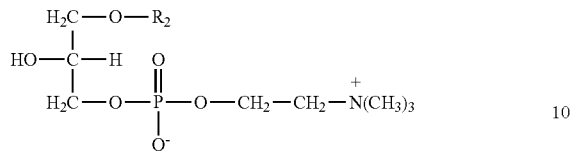
wherein, $R_2$ is $C_{4-30}$ alkyl, or $C_{4-30}$ alkenyl having one or more double bonds.
3. The lipid nanomaterial of claim 1, wherein the lipid nanomaterial is nanoparticles having a size of 1-1000 nm.
* * * * *